United States Patent

Gras et al.

[11] Patent Number: 5,556,937
[45] Date of Patent: Sep. 17, 1996

[54] SALTS OF PYROMELLITIC ACID, A PROCESS FOR THEIR PREPARATION, AND THEIR USE

[75] Inventors: Rainer Gras, Bochum; Elmar Wolf, Recklinghausen; both of Germany

[73] Assignee: Huels Aktiengesellschaft, Marl, Germany

[21] Appl. No.: 365,422

[22] Filed: Dec. 28, 1994

[30] Foreign Application Priority Data

Jan. 14, 1994 [DE] Germany ............. 44 00 931.3

[51] Int. Cl.$^6$ ............. C08G 69/00; C08F 20/00
[52] U.S. Cl. ............. 528/288; 528/93; 528/113; 528/114; 528/119; 528/422; 525/438; 525/533; 525/934
[58] Field of Search ............. 525/438, 533, 525/934; 528/93, 113, 114, 119, 288, 369, 422

[56] References Cited

U.S. PATENT DOCUMENTS

| | | | |
|---|---|---|---|
| 3,947,384 | 3/1976 | Schulde et al. | 427/27 |
| 4,007,299 | 2/1977 | Schulde et al. | 427/195 |
| 4,130,510 | 12/1978 | Tanaka et al. | 528/114 |
| 4,455,426 | 6/1984 | Meyer et al. | 544/253 |
| 4,943,516 | 7/1990 | Kamayachi et al. | 430/280 |
| 5,310,818 | 5/1994 | Tojo et al. | 525/348 |

FOREIGN PATENT DOCUMENTS 1900825  8/1970  Germany.

Primary Examiner—John C. Bleutge
Assistant Examiner—Randy Gulakowski
Attorney, Agent, or Firm—Oblon, Spivak, McClelland, Maier & Neustadt, P.C.

[57] ABSTRACT

The invention relates to salts of pyromellitic acid which comprise 1 mol of pyromellitic acid and 0.5. to 2 mol of a guanidine of the following composition:

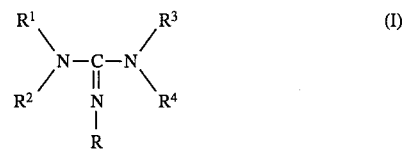

in which R, $R^1$, $R^2$, $R^3$ and $R^4$ are identical or different radicals from the group consisting of hydrogen, alkyl, cycloalkyl and aromatic hydrocarbon residues having 1 to 8 carbon atoms, and $R^1$ and $R^2$ and $R^3$ and $R^4$ may form a joint ring which may contain an oxygen atom as heteroatom. Also claimed are the preparation of the salts and their use for matt epoxide and hybrid powder coatings.

4 Claims, No Drawings

SALTS OF PYROMELLITIC ACID, A PROCESS FOR THEIR PREPARATION, AND THEIR USE

BACKGROUND OF THE INVENTION

1. Field of the Invention

The invention relates to new salts of pyromellitic acid, to a process for their preparation and to their use for the production of matt epoxide and hybrid powder coatings.

2. Discussion of the Background

Pyromellitic acid is conventionally used in matt epoxide and hybrid powder coatings. For example, U.S. Pat. No. 3,947,384 and U.S. Pat. No. 4,007,299 describe processes for the production of matt coatings, in which epoxy resins are cured using salts of pyromellitic acid and cyclic amidines (imidazolines, tetrahydropyrimidines). Unfortunately, such resin requires temperatures of 180° C. to 200° C. for curing.

Curing agents having the advantageous properties of the pyromellitic acid salts of U.S. Pat. No. 3,947,384 and U.S. Pat. No. 4,007,299 and which can be cured at about 20° C. or lower, which is not currently possible, are desirable.

SUMMARY OF THE INVENTION

Accordingly, one object of the present invention is to provide a curing agent having the advantageous properties of the pyromellitic acid salts of U.S. Pat. No. 4,007,299 and U.S. Pat. No. 3,947,384 and which can be cured at about 20° C. or lower.

Surprisingly, the present inventors have achieved this object by using guanidine salts of pyromellitic acid.

The present invention therefore relates to salts of pyromellitic acid which comprise 1 mol of pyromellitic acid and 0.5 to 2 mol of a guanidine of the formula (I):

$$\begin{array}{c} R^1 \\ \diagdown \\ R^2 \end{array} N-\underset{\underset{R}{\overset{\|}{N}}}{C}-N \begin{array}{c} R^3 \\ \diagup \\ R^4 \end{array} \qquad (I)$$

wherein R, $R^1$, $R^2$, $R^3$ and $R^4$, identical or different, are each a radical selected from the group consisting of hydrogen, $C_{1-8}$ alkyl, $C_{3-8}$ cycloalkyl and $C_{6-8}$ aryl, or $R^1$ and $R^2$ and $R^3$ and $R^4$ may jointly form a $C_{3-8}$ alkyl ring in which one of the carbon atoms may be substituted with an oxygen atom.

DETAILED DESCRIPTION OF THE PREFERRED EMBODIMENTS

Pyromellitic acid, also 1,2,4,5-benzenetetracarboxylic acid, is available commercially, for example from Aldrich (Milwaukee, Wis.).

Preferred guanidines of the formula (I) in accordance with the present invention include tetramethylguanidine, tetramethylcyclohexylguanidine, N,N',N"-triphenylguanidine and N,N'dicyclohexyl-4-morpholinecarboxamide.

Suitable guanadine salts of pyrometallic acid according to the present invention have a basic nitrogen content of 1 to 10 mmol of $NH_2/$ g and a carboxyl group content of 3 to 13 mmol/g.

The salts of pyromellitic acid according to the invention are substances which range from colourless to—in some cases—intense yellow in colour, having melting points of from 140° up to about 250° C.

The salts of pyromellitic acid according to the present invention can be prepared by any conventional manner. For example, guanidine salts can be prepared by adding the guanidine component in portions to the pyromellitic acid, dissolved in water or ethanol, at the boiling temperature. After the addition of guanidine is complete, heating is continued for about 1 hour more. The mixture is then cooled to room temperature.

In ethanol, the precipate which is formed is filtered off and is dried, for example, at 60° C. in a vacuum drying cabinet.

In water, the reaction product is soluble. The water can be removed by known methods, for example by distillation or spray drying.

In a second embodiment, the invention relates to a process for the preparation of salts of pyromellitic acid comprising reacting 1 mol of pyromellitic acid with 0.5 to 2 mol of a guanidine in $H_2O$ and/or ethanol at 50° to 100° C. and, after the reaction has finished, freeing the reaction product from the solvent or isolating it by spray drying.

In a third embodiment, the salts of pyromellitic acid according to the present invention can be used to produce matt epoxide and hybrid powder coatings. As already mentioned, the guanidine salts of pyromellitic acid according to the invention are suitable for the production of matt epoxide and hybrid powder coatings, as described in, for example, U.S. Pat. No. 3,947,382 and U.S. Pat. No. 4,007,299.

Suitably for matt hybrid epoxide powder coatings, the epoxy resin contains (i) 0.5 to 12% by weight, preferably 1 to 7% by weight, particularly preferably 2.0 to 5.5% by weight, of the salts of pyromellitic acid according to the present invention; (ii) a COOH-containing polyester; and, if desired, (iii) an isophorone diisocyanate adduct blocked with ε-caprolactam.

Suitably for matt epoxide powder coatings, the epoxy resin contains 3 to 12% by weight, preferably 4 to 7% by weight, of the salts of pyromellitic acid according to the present invention.

Suitable epoxide resins are solid, resinous substances which melt in the range 60° to 150° C., preferably 70° to 110° C., and which contain on average more than one 1,2-epoxide group per molecule. In principle, all compounds are suitable which contain more than one 1,2-epoxide group per molecule; however, preference is given to commercially available epoxy resins as are obtained by reaction of bisphenol A and epichlorohydrin, having an epoxide equivalent weight of 400 to 3000, preferably 800 to 1000.

The carboxyl group-containing polymers are polyester-polycarboxylic acids which are prepared from polyols and polycarboxylic acids and/or their derivatives. The melting range of these acidic polyesters is 60° to 160° C., preferably 80° to 120° C.; their acid number varies from 10 to 150 mg of KOH/g, preferably 30 to 60 mg of KOH/g. The OH numbers should be below 10 mg of KOH/g.

Examples of the polycarboxylic acids to be employed for the preparation of the polyester-polycarboxylic acids to be used in accordance with the invention are oxalic, adipic, 2,2,4-(2,4,4-)trimethyladipic, azelaic, sebacic, decanedicarboxylic, dodecanedicarboxylic, fumaric, phthalic, isophthalic, terephthalic, trimellitic and pyromellitic acid. The polyols used for the acidic polyesters are as follows: ethylene glycol, 1,2- and 1,3-propanediol, 1,2-, 1,3-, 1,4- and 2,3-butanediol, 1,5pentanediol, 3-methyl-1,5-pentanediol, neopentylglycol, 1,6-hexanediol, 1,12-dodecanediol, 2,2,4-(2,4,4-)-trimethyl-1,6-hexanediol, trimethylolpropane, glycerol, pentaerythritol, 1,4-bis-hydroxymethylcyclohexane, cyclohexane-1,4-diol, diethylene glycol, triethylene glycol and dipropylene glycol. It is of course also possible to react polyesters which contain hydroxyl groups, and which are prepared by known methods from polycarboxylic acids and polyols, with polycarboxylic acids and/or polycarboxylic acid anhydrides to give the polyester-polycarboxylic acids.

When present, the isophorone diisocyanate adducts blocked with ε-caprolactam is used in amounts 0.1 to 0.5 NCO equivalents per 1 OH equivalent of the epoxy resin. Any solid (cyclo)aliphatic polyisocyaates can be used in accordance with the present invention as polyisocyanates. The solid, blocked as well as unblocked polyol-isophorone diisocyanate adducts (OH: NCO=1:2) as well as the trimeric (isocyanurate) of isophorone diisocyanate are particularly suitable. The mean molar weight of the polyisocyanate is 450 to 1,200, preferably 800 to 1,000.

The quantities of the individual powder coating binder components can be varied substantially.

In the case where commercially available epoxy resins based on bisphenol A (plus epichlorohydrin) are used exclusively (matt epoxide powder coatings), the concentration of curing agent is 3 to 12%. In the case where mixtures are used of epoxy resins of the bisphenol A diglycidyl ester and carboxyl group-containing polyester type (matt hybrid epoxide powder coatings), the proportion depends on the acid number of the carboxy polyester. For example, for an acid number of 30 to 50 mg of KOH/g, the weight ratio of epoxy resin to carboxy polyester is usually from 60:40 to 80:20, preferably 70:30. The concentration of the salts according to the invention in these epoxy resin/carboxy polyester mixtures is 0.5 to 12% by weight.

For the production of the powder coating, the binders are first mixed together with the levelling agent, pigment and the UV and oxidation stabilizers and homogenized in an extruder at 80° to 130° C. as described in DE 3328130. After cooling to room temperature, the extrudate is ground to give a powder coating whose average particle size is preferably about 40 to 80 μm, particularly preferably 50 μm.

The application of the powder coatings thus produced to appropriate substrates can be carried out by the known processes, for example by electrostatic powder spraying or fluidized-bed sintering. Following the application of the powder coating by one of the processes mentioned, the coated substrates are heated at temperatures of 150° to 220° C. over periods from 30 to 6 min, for purposes of curing. The coating films thus produced are distinguished by very good levelling, outstanding solvent resistance and a matt surface, it being possible to adjust the degree of gloss as desired within a wide range.

Having generally described this invention, a further understanding can be obtained by reference to certain specific examples which are provided herein for purposes of illustration only and are not intended to be limiting unless otherwise specified.

EXAMPLES

I. Preparation of the salts according to the invention
   General preparation procedure
   The salts of pyromellitic acid listed in the following table were prepared as follows:
   The amine was added dropwise to a solution of pyromellitic acid in water. When the addition of amine was complete, heating was continued for about 1 h more (at 60° to 80° C.) after which the water was removed by distillation. For complete removal of the water, drying was carried out at 80° C. in a vacuum drying cabinet.

| Example I. | Pyromellitic acid (mol) | mol | Amin | Melting (°C.) | NH₂ (mmol/g) | COOH (mmol/g) |
|---|---|---|---|---|---|---|
| 1 | 1 | 1 | HN=C−(N(CH₃)₂)₂ | 183–187 | 2,610 | 10,693 |
| 2 | 1 | 2 | HN=C−(N(CH₃)₂)₂ | 210–217 | 4,004 | 8,211 |
| 3 | 1 | 3 | 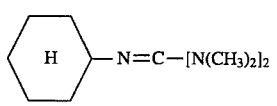 | 205–216 | 2,481 | 9,816 |
| 4 | 1 | 4 | 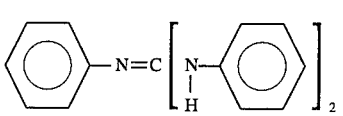 | 218–231 | 1,842 | 6,823 |

II. Epoxy resin

In the application examples, the epoxy resin compound employed was one based on bisphenol A. It has the following characteristics:

| Example Characteristics | II.1 |
|---|---|
| equivalent weight | 900–1000 |
| epoxide value | 0.1–0.111 |
| hydroxyl value | 0.34 |
| melting range | 96–104° C. |

III. Epoxy resin powder coatings

For the production of the powder coatings the ground products—curing agent, epoxy resin and levelling agent masterbatch[1]—were intimately mixed with the homogenized in an extruder at from 90° to 110° C. After cooling the extrudate was fractionated and was ground in a pin mill to a particle size<100 μm. The powder thus produced was applied, using an electrostatic powder spraying unit at 60 kV, to degreased and—if appropriate—pretreated steel panels which were baked in a circulating-air laboratory drying cabinet.

[1]Levelling masterbatch 10% by weight of levelling agent based on polymeric butyl acrylates is homogenized in the melt with the epoxy resins and is comminuted after solidifying.

The abbreviations in the following tables denote:

| | |
|---|---|
| LT = layer thickness (μm) | |
| CH = cross hatch test | (DIN 53 151) |
| EI = Erichsen indentation (mm) | (DIN 53 156) |
| GG 60° ≮ = Gardner gloss | (ASTM-D 523) |
| Imp. rev. = Impact reverse (g · m) | |

The calculation of the coating formulations was made in accordance with the following scheme:

| |
|---|
| % by weight EP = epoxide |
| B − C = EP B = % by weight binder |
| C = % by weight crosslinking agent |
| B = 100 − A  A = % by weight additives |
| [40% by weight white pigment (TiO$_2$), |
| 0.5 by weight of levelling agent] |

| Example III | Crosslinking agent % by wt. | acc. to | Curing °C./min | | LT | CH | EI | Imp. rev. | GG 60° ≮ |
|---|---|---|---|---|---|---|---|---|---|
| 1 | 4 | I.1 | 200 | 12 | 60–65 | 0 | 5 | 115.2 | 4 |
| | | | | 15 | 60–65 | 0 | 7–7.1 | 230.4 | 4 |
| | | | 180 | 20 | 60–70 | 0 | 5.1–5.4 | 115.2 | 5 |
| | | | | 25 | 55–60 | 0 | 8.0–8.2 | 230.4 | 5 |
| | | | 170 | 25 | 60–70 | 0 | 6.2–7.3 | 115.2 | 6 |
| 2 | 5 | I.1 | 200 | 12 | 65–70 | 0 | 6.5–7.8 | 345.6 | 4 |
| | | | | 15 | 50–65 | 0 | 7.8–8.0 | 460.8 | 4 |
| | | | 180 | 15 | 60–80 | 0 | 3.1–5.6 | 115.2 | 5 |
| | | | | 20 | 50–60 | 0 | 7.4–7.9 | 230.4 | 4 |
| | | | 170 | 25 | 50–65 | 0 | 5.2–5.5 | 115.2 | 5 |
| 3 | 5.5 | I.1 | 200 | 12 | 50–60 | 0 | 7.5–8.1 | 230.4 | 4 |
| | | | 180 | 15 | 50–60 | 0 | 5.0–6.1 | 230.4 | 4 |
| | | | 170 | 25 | 55–65 | 0 | 6.4–6.9 | 115.2 | 5 |
| | | | 160 | 30 | 50–60 | 0 | 5.5–6.5 | 115.2 | 6 |
| 4 | 6 | I.1 | 180 | 15 | 65–70 | 0 | 5.6–6.5 | 115.2 | 5 |
| | | | 170 | 20 | 55–60 | 0 | 5.7–6.0 | 115.2 | 5 |
| | | | | 25 | 60–65 | 0 | 6.2–6.7 | 115.2 | 5 |
| | | | 169 | 30 | 50–60 | 0 | 5.6–5.9 | <115.2 | 7 |
| | | | | 35 | 45–55 | 0 | 6.0–7.1 | 345.6 | 7 |

IV. Carboxyl group-containing polyester

For the production of hybrid powder coatings, the carboxyl group-containing polyesters described below were employed, having the following characteristics:

| | I | II |
|---|---|---|
| Acid number: | 52–58 mg of KOH/g | 36 mg of KOH/g |
| Melting range: | 104–106° C. | 91–94° C. |
| Glass transition Temperature: | about 58° C. | 64° C. |
| Viscosity at 160° C.: | 33,400 mpa · s | 58,000 mpa · s |

V. Hybrid powder coatings

The processing of the raw materials, the preparation and application were carried out in analogy to III.

EXAMPLE 1

In accordance with the method described, the powder coating with the following formulation was prepared, applied and baked at between 170° C. and 200° C.

390.0 parts by wt. of epoxide according to II.1

75.0 parts by wt. of crosslinking agent according to I.1

400.0 parts by wt. of white pigment (TiO$_2$)

50.0 parts by wt. of levelling agent masterbatch 75.0 parts by wt. of polyester according to IV.1

| Baking conditions | | Mechanical characteristics | | | | |
|---|---|---|---|---|---|---|
| Time/ min | temp. °C. | LT | CH | EI | Imp. rev. | GG 60° ≮ |
| 10 | 200 | 70–80 | 0 | 4.1–4.4 | 115.2 | 20 |
| 15 | | 60–70 | 0 | 4.0–4.2 | 230.4 | 20 |
| 20 | | 70–90 | 0 | 4.0–4.4 | 115.2 | 20 |
| 20 | 180 | 60–70 | 0 | 3.7–4.2 | 115.2 | 19 |
| 30 | | 50–60 | 0 | 4.1–5.0 | 115.2 | 18 |
| 25 | 175 | 65–80 | 0 | 4.3–5.0 | 115.2 | 17 |
| 30 | | 50–60 | 0 | 6.2–6.6 | 115.2 | 18 |

EXAMPLE 2

In accordance with the method described, the powder coating with the following formulation was prepared, applied and baked at between 180° C. and 200° C.

350.0 parts by wt. of epoxide according to II.1

55.0 parts by wt. of crosslinking agent according to I.1

400.0 parts by wt. of white pigment (TiO$_2$)

50.0 parts by wt. of levelling agent masterbatch 145.0 parts by wt. of polyester according to IV.1

| Baking conditions | | Mechanical characteristics | | | | |
|---|---|---|---|---|---|---|
| Time/ min | temp. °C. | LT | CH | EI | Imp. rev. | GG 60° ≮ |
| 10 | 200 | 70–80 | 0 | 5.9–6.1 | 651.2 | 23 |
| 15 | | 80–90 | 0 | 6.3–7.0 | 460.8 | 25 |
| 20 | | 90 | 0 | 7.0–7.3 | 460.8 | 27 |
| 20 | 180 | 80–90 | 0 | 6.3–6.8 | 345.6 | 25 |
| 30 | | 70–85 | 0 | 7.1–7.6 | 460.8 | 24 |

|  |  |  |  |  |  |  |  |  | GG |
|---|---|---|---|---|---|---|---|---|---|
|  | Formulation |  | Curing |  |  |  |  | Imp. | 60° |
| Example V | % by wt. | acc. to | °C./min |  | LT | CH | EI | rev. | < |
| 3 | 10 | I.1 | 200 | 10 | 60–70 | 0 | 3.9–4.5 | 115.2 | 42 |
|  | 273 | II.1 |  | 15 | 50–70 | 0 | >10 | 345.6 | 45 |
|  | 267 | IV.2 | 180 | 20 | 60–65 | 0 | 4.4–4.9 | 115.2 | 55 |
|  | 400 | white |  | 25 | 50–60 | 0 | >10 | 230.4 | 51 |
|  |  | pigment (TiO$_2$) | 170 | 25 | 60–65 | 0 | 3.8–4.2 | <115.2 | 53 |
|  | 50 | level. MB |  |  |  |  |  |  |  |
| 4 | 30 | I.1 | 200 | 10 | 55–70 | 0 | 8.4 | 115.2 | 13 |
|  | 312 | II.1 |  | 15 | 60–70 | 0 | 9.8 | 345.6 | 13 |
|  | 208 | IV.2 | 180 | 20 | 55–70 | 0 | 6.9 | 230.4 | 13 |
|  | 400 | white |  | 25 | 55–65 | 0 | 9.2 | 345.6 | 13 |
|  |  | pigment (TiO$_2$) | 170 | 25 | 60–70 | 0 | 5.4 | 230.4 | 15 |
|  | 50 | level. MB |  |  |  |  |  |  |  |
| 5 | 50 | I.1 | 200 | 10 | 50–60 | 0 | 5.3 | 115.2 | 10 |
|  | 352 | II.1 |  | 15 | 65–70 | 0 | 8.5–8.9 | >944.6 | 12 |
|  | 148 | IV.2 | 180 | 20 | 50–70 | 0 | 6.4 | 115.2 | 10 |
|  | 400 | white |  | 25 | 50–80 | 0 | 7.8–8.5 | 806.4 | 10 |
|  |  | pigment (TiO$_2$) | 170 | 25 | 50–65 | 0 | 6.5 | <115.2 | 11 |
|  | 50 | level. MB |  |  |  |  |  |  |  |

Having now fully described the invention, it will be apparent to one of ordinary skill in the art that many changes and modifications can be made thereto without departing from the spirit or scope of the invention as set forth herein.

What is claimed and new and desired to be secured by letters patent of the United States is:

1. A salt of pyromellitic acid comprising:

1 mol of pyromellitic acid; and 0.5–2 mol of a guanidine of the formula (I):

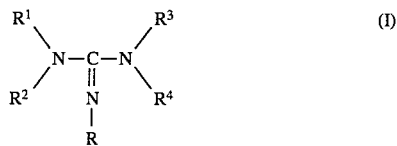

wherein R, R$^1$, R$^2$, R$^3$ and R$^4$, identical or different, are each a radical selected from the group consisting of hydrogen, C$_{1-8}$ alkyl, C$_{3-8}$ cycloalkyl and C$_{6-8}$ aromatic hydrocarbon residues, or R$^1$ and R$^2$ and R$^3$ and R$^4$ may jointly form a ring containing 5 to 7 carbon atoms in which one of the carbon atoms may be substituted with an oxygen atom.

2. The salt of pyromellitic acid of claim 1, wherein R$^1$, R$^2$, R$^3$ and R$^4$ are each methyl and R is hydrogen or cyclohexyl.

3. The salt of pyromellitic acid of claim 1, wherein R is benzene, R$^1$ and R$^3$ are benzene and R$^2$ and R$^4$ are hydrogen.

4. A process for preparing a salt of pyromellitic acid comprising 1 mol of pyromellitic acid and 0.5 to 2 mol of a guanidine of the formula (I):

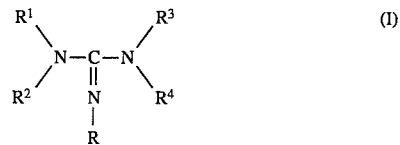

wherein R, R$^1$, R$^2$, R$^3$ and R$^4$, identical or different, are each a radical selected from the group consisting of hydrogen, C$_{1-8}$ alkyl, C$_{3-8}$ cycloalkyl and C$_{6-8}$ aromatic hydrocarbon residues, or R$^1$ and R$^2$ and R$^3$ and R$^4$ may jointly form a ring containing 3 to 8 carbon atoms in which one of the carbon atoms may be substituted with an oxygen atom; comprising the steps of:

reacting 1 mol of pyromellitic acid with 0.5–2 mol of a guanidine in H$_2$O, ethanol or a mixture thereof at 50–100° C.; and after reaction has finished, isolating said guandine salt of pyromellitic acid from the solvent.

* * * * *